United States Patent [19]
Albert

[11] 4,116,236

[45] Sep. 26, 1978

[54] KNEE BRACE WITH KNEECAP-ENCIRCLING FLEXIBLE RESILIENT PAD

[75] Inventor: William J. Albert, Cincinnati, Ohio

[73] Assignee: Surgical Appliance Industries, Inc., Cincinnati, Ohio

[21] Appl. No.: 768,031

[22] Filed: Feb. 14, 1977

[51] Int. Cl.$^2$ .............................................. A61F 3/00
[52] U.S. Cl. ....................................... 128/80 C; 2/24
[58] Field of Search ................... 128/80 C, 165; 2/22, 2/24

[56] References Cited

U.S. PATENT DOCUMENTS

| | | | |
|---|---|---|---|
| 2,195,024 | 3/1940 | Bullock | 128/80 C X |
| 3,046,981 | 7/1962 | Biggs, Jr. et al. | 128/80 C |
| 3,074,400 | 1/1963 | Schulman | 128/165 |
| 3,084,685 | 4/1963 | Lewis | 128/80 C |

FOREIGN PATENT DOCUMENTS

433,715  9/1925  Fed. Rep. of Germany ................ 2/24

*Primary Examiner*—John D. Yasko
*Attorney, Agent, or Firm*—Wood, Herron & Evans

[57] ABSTRACT

A knee brace including an elastic sleeve stretchable only in a circumferential direction having an opening in the front thereof for accommodating the kneecap of a wearer when in knee-encircling relation thereto. A resilient flexible circumferentially relatively inelastic annular, or alternatively inverted U-shaped, pad is loosely mounted to the interior of the elastic sleeve in the region generally surrounding the kneecap opening with the upper and opposite sides of the pad adjacent at least the top and opposite sides of the sleeve kneecap opening, respectively, to limitedly variably positionably locate the pad relative to the sleeve kneecap opening to permit the pad to self-align centrally of the wearer's kneecap notwithstanding limited misalignment between the sleeve kneecap opening and the wearer's kneecap. The circumferential relatively inelasticity of the resilient pad, particularly the portion thereof which is integral with the pad side sections, resists rearward movement and dislocation relative to the wearer's kneecap of the opposite side pad sections when the wearer's knee is flexed. Flat helical spring stays located exteriorly of the elastic sleeve and confined by inelastic fabric pockets sewn to the exterior of the sleeve are positioned over the side portion of the pad between side edges of the kneecap and the ligaments located in the side of the knee to enhance the compression applied to the knee when the knee is flexed.

14 Claims, 10 Drawing Figures

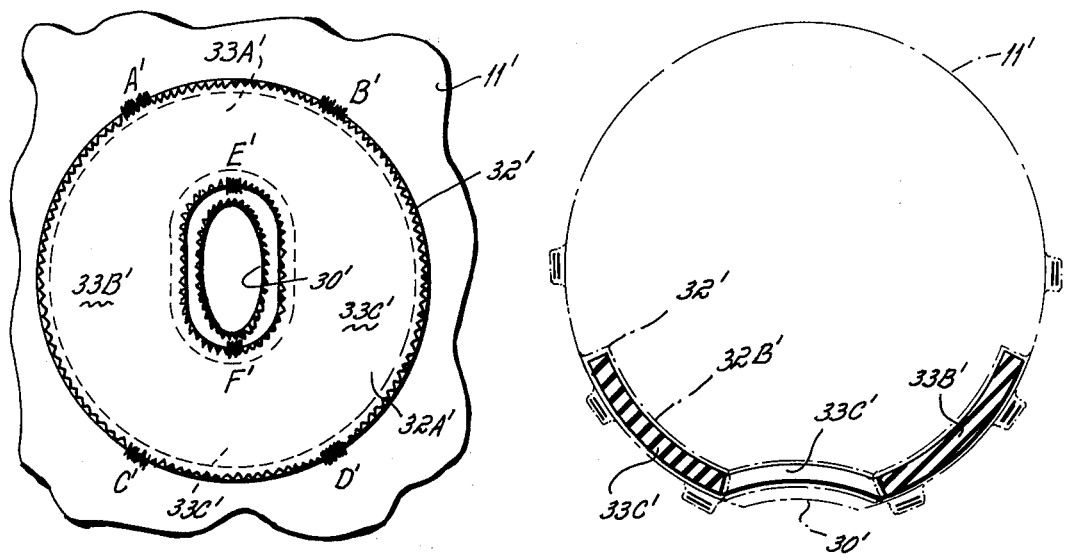
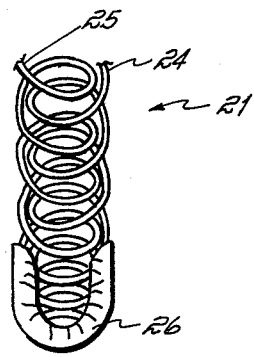
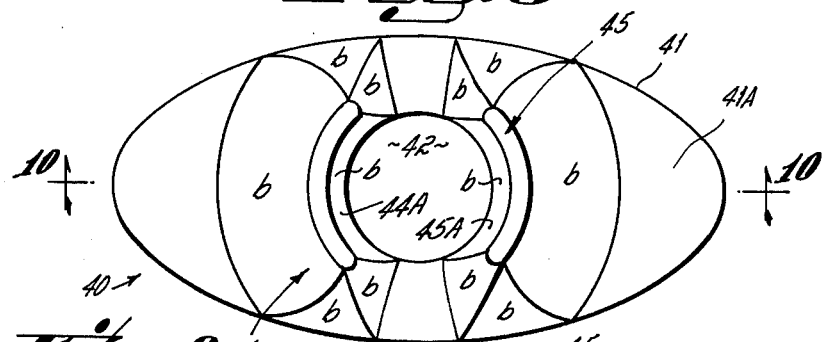
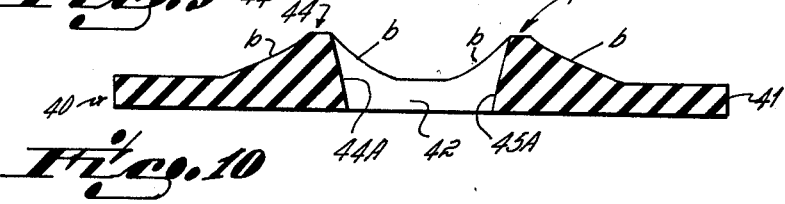

KNEE BRACE WITH KNEECAP-ENCIRCLING FLEXIBLE RESILIENT PAD

This invention relates to a knee brace of the type adapted to support an injured or weakened knee joint, and is particularly directed to an improvement of the knee brace disclosed and claimed in U.S. Pat. No. 3,084,685 in the name of Hector E. Lewis entitled "Knee Brace."

In one form of the invention disclosed and claimed in the above-identified patent, a knee brace is provided comprising an elastic sleeve stretchable only in a circumferential direction adapted to fit over the leg area at the knee and carrying a plurality of longitudinal or vertical pockets adapted to receive elongated pressure elements. The pressure elements are in the form of flat helical springs which are interleaved and overlapped so that the pressure members can be deformed in a transverse plane, but resist elongation. The pockets are formed of an inelastic material extending substantially the full length of the sleeve and the springs are of substantially the same length as the length of the pockets. The sleeve is provided with an opening disposed over the wearer's kneecap, and positioned interiorly of the kneecap on either side of the opening and mounted in pockets stitched to the inside of the sleeve beneath the springs, are two tapered resilient pads. The pads are positioned to overlie the lateral joint space of the knee area.

When the knee is in a straight position, the spring pressure members function to rigidify the sleeve and to apply increased pressure over the ligament areas. When the knee is bent, the springs conformed to the shape of the knee and therefore remain in contact with the knee over the ligament areas. The springs and their inelastic pockets, which are disposed over the front and the side areas of the knee, are placed in tension when the knee is bent. Since the pockets are inelastic and cannot appreciably stretch, the tension force is transmitted through the springs to the ligament areas. Also, shifting of the springs within the pockets is effectively resisted by friction so that the tension of the springs themselves augments the force applied to the ligaments.

While the springs not only provide a generally conforming pressure over the entire joint area, by virtue of the pads disposed thereunder on either side of the kneecap, the springs exert pressure of relatively high concentration in localized areas across the joint space. This pressure is applied directly to the site of potential injury, i.e., the cartilage area; and is effective to prevent lateral or medical rotation at the joint as well as anterior or posterior glide and protrusion of the lateral or medial cartilages. Additionally, the pads and encircling circumferentially stretchable eleastic sleeve provide some resistance to complete flexion of the knee which might be injurious under some circumstances.

The knee brace disclosed and claimed in the above-identified application and described briefly above has, over the years, proven to be enormously effective in protecting the knee against injury and enhancing post-operative recovery from certain types of knee operations. However, two areas for improvement, with respect to which the present invention is directed, have been observed. One such problem relates to the tendency of the resilient pads located on either side of the kneecap interiorly of the elastic sleeve to move rearwardly and dislocate relative to the sides of the kneecap when the knee is flexed. Accordingly, in accordance with certain principles of this invention the foregoing problem is overcome by substituting, for the separate pads located on either side of the kneecap interior of the elastic sleeve, a single pad which is either annular or in the form of an inverted U in shape. The unitary pad, while being flexible and resilient, is relatively inelastic in a knee-embracing circumferential direction when compared to the relatively high elasticity of the sleeve in a circumferential direction. As a consequence, and by virtue of the fact that the relatively inelastic upper section of the pad (which overlies the upper portion of the kneecap) is integral with the sides of the pad, the upper portion of the pad retains the side portions of the pad in position adjacent the sides of the kneecap when the knee is flexed. Thus, the localized pressure and protection for the kneecap which the resilient pad provides when the knee is straight is not decreased when the knee is moved from a straight position to a flexed position.

A second area of improvement of the kneecap disclosed and claimed in the above-identified patent relates to obtaining correct positioning of the pads located on either side of the kneecap interiorly of the elastic sleeve when the sleeve is placed over the knee and the wearer fails to properly align the knee opening in the sleeve with his kneecap. With the knee brace disclosed and claimed in the above-identified application, the resilient pads on either side of the kneecap interiorly of the elastic sleeve had a tendency to become misaligned or asymmetrically disposed relative to the kneecap if the wearer's kneecap was not aligned and symmetrical with the opening in the sleeve thereof designed to accommodate the kneecap. As a consequence, when the wearer did not locate the knee brace properly such that the kneecap opening in the sleeve was centrally disposed relative to the kneecap, the resilient pads on either side of the kneecap interiorly of the sleeve did not automatically symmetrically position themselves on either side of the kneecap.

Accordingly, with the knee brace of this invention it has been possible to self-align and symmetrically dispose resilient pads on either side of the kneecap notwithstanding some misalignment between the kneecap and the kneecap opening provided in the elastic sleeve. This has been accomplished in accordance with certain additional principles of the invention by providing means to loosely mount the annular, or inverted C-shaped pad, in the interior of the sleeve in the region generally surrounding the kneecap opening, with the upper and opposite side of the pad adjacent at least the top and side of the opening, respectively. This "loose mounting" of the pad in the interior of the sleeve has the effect of limitedly variably positionally locating the pad relative to the sleeve kneecap opening, permitting the pad to self-align centrally of the wearer's kneecap notwithstanding limited misalignment between the kneecap opening and the wearer's kneecap.

In a preferred form the means to loosely mount the pad relative to the sleeve kneecap opening takes the form of a flexible interior pocket disposed in the interior of the sleeve surrounding the kneecap opening adjacent at least the top and sides thereof. The flexible pocket has inner and outer peripheral edges which are secured to the sleeve at spaced points along the periphery thereof. The points at which the interior pocket is secured to the sleeve selectively constitute a small fraction of the peripheral edge of the pocket available for securement to the sleeve. As a consequence, the pad is positionably shiftable relative to the sleeve kneecap opening to permit the pad to self-align centrally of the wearer's kneecap notwithstanding limited misalignment between the kneecap opening and the wearer's kneecap.

These and other objects, advantages and features of the invention will become more readily apparent from a detailed description of two preferred embodiments thereof taken in connection with the drawings in which:

FIG. 6 is an elevational view of the interior of a second preferred embodiment of the knee brace of this invention utilizing an annular resilient pad designed to surround the entirety of the wearer's kneecap when in use;

FIG. 7 is a cross-sectional view similar to that of FIG. 5 of a knee brace incorporating the annular resilient kneecap-surrounding pad shown in FIG. 6;

FIG. 8 is a partial fragmentary view of a spring pressure element used in conjunction with the braces of this invention;

FIG. 9 is an elevational view of a further modification of a resilient pad suitable for loose mounting interiorly of the elastic sleeve proximate the sleeve kneecap opening; and FIG. 10 is a cross-sectional view taken along line 10—10 of FIG. 9.

Figure 1:
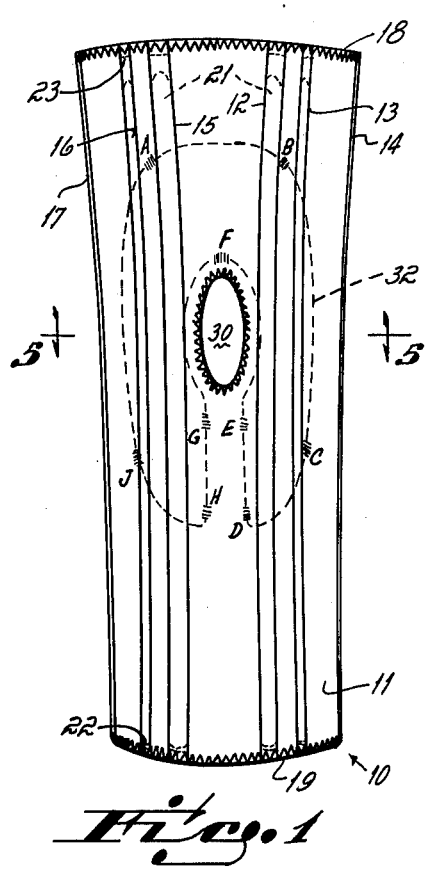
FIG. 1 is a front elevational view of one preferred embodiment of the invention utilizing an inverted U-shaped pad surrounding a substantial portion of the kneecap.
Figure 2:
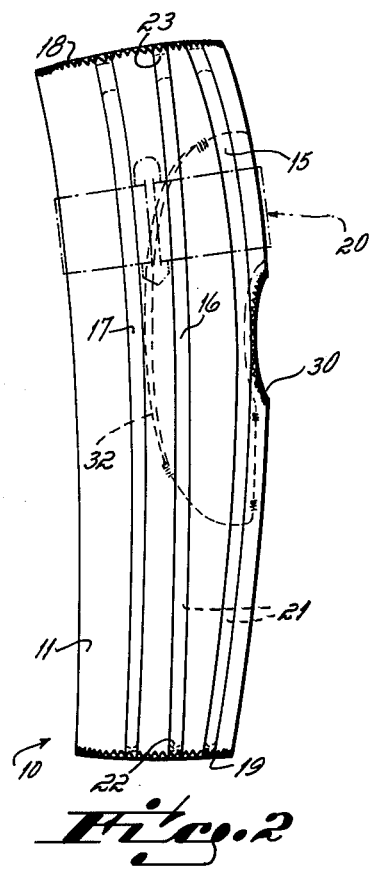
FIG. 2 is a side elevational view of the knee brace shown in FIG. 1.
Figure 4:
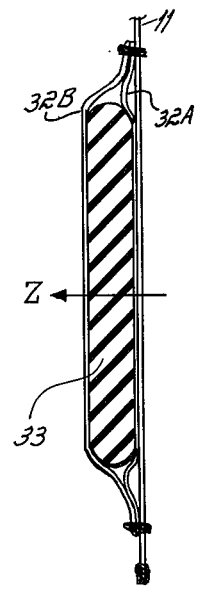
FIG. 4 is a cross-sectional view taken along line 4—4 of FIG. 3.
Figure 3:
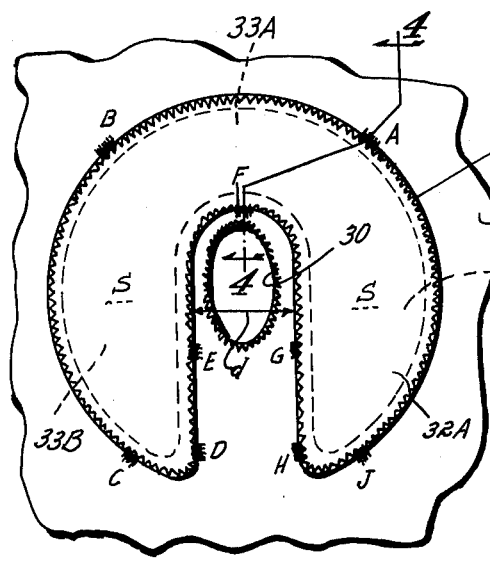
FIG. 3 is an elevational view of a portion of the knee brace of FIG. 1 showing the interior thereof in the region of the inverted U-shaped resilient pad.

As shown in FIGS. 1-5, one form of the kneecap, or brace, 10 constructed in accordance with the present invention comprises a sleeve member 11 preferably formed of woven relatively highly elastic material which is stretchable only in a circumferential direction. Sleeve 11 preferably tapers slightly from the top to bottom and is slightly curved, the front surface thereof being convex, to conform to the contour of the knee. Sleeve 10 has secured to its exterior surface a plurality of longitudinal pocket-forming strips 12-17. Strips 12-17 are formed of a thin nonelastic material and in the preferred embodiment of FIGS. 1-5 extend from the upper edge 18 to the lower edge 19 of the sleeve. The pockets defined by strips 12-14 are disposed to overlie and engage portions of the wearer's knee extending from the righthand edge of the kneecap to the ligaments running along the side of the knee as shown in FIG. 2. Each of the strips 12-14 is parallel to the other strips 15-17 of the righthand side of the brace 10. Strips 15, 16, and 17 are disposed to overlie the right side of the knee from the ligaments adjacent to the right edge of the kneecap to the ligaments of the rear righthand side of the knee.

Each of the pockets is stitched to the sleeve 11 and confines an elongated pressure element 21. Each of the pressure elements extends substantially the full length of the pocket, for example, from the bottom stitch line 22 to the top stitch line 23 of pocket 16. Each of the pressure elements 21 is a flat member which initially can be flexed in any transverse direction, or twisted, but which resists elongation.

More particularly, each pressure member 21 comprises one or more flattened helical spring elements. In a preferred embodiment, each member 21 comprises two component springs 24 and 25. The springs are interleaved and are overlapped as shown in FIG. 8. Each of the pressure elements is provided with a generally U-shaped cap 26 in the form of a channel element which receives the ends of the helical spring elements. Caps 26 are compressed tightly against the spring elements to hold them in assembled relation.

An opening 30 is provided in the front section of the sleeve 11 to accommodate the wearer's kneecap when the sleeve is positioned about the wearer's knee. Inside the brace adjacent to the top and opposite sides of the opening 30 is a pocket 32 which is generally in the form of an inverted U-shape. The pocket 32 is formed by stitching two generally inverted U-shaped pieces of fabric 32A and 32B to each other along their inner and outer peripheries, the two fabric pocket-forming pieces being placed in overlying face-to-face confronting relation to each other. The pocket-forming fabric pieces 32A and 32B are preferably fabricated of elastic material stretchable only in a leg encircling, circumferential direction.

Located within the pocket 32 is a flexible resilient pad 33 which, like the pocket 32, is generally in the form of an inverted U-shape. The pad is of one piece construction having integral upper section 33A and opposite side sections 33B and 33C adjacent the upper and opposite sides of the kneecap opening 30 in the sleeve 11. While the pad 33 is flexible and resilient, it is constructed to have relatively little elasticity in a circumferential, or knee encircling, direction when compared to the elasticity of the sleeve 11 in the same direction. As a consequence, the side sections 33B and 33C of the pad 33 do not move significantly rearwardly, or dislocate relative to the kneecap, when the knee is flexed. More particularly, it is the upper section 33A of the one-piece pad 33 which, when the knee is flexed, prevents the side sections 33B and 33C of the pad 33, particularly the upper regions thereof, from dislocating or moving rearwardly when the knee is flexed. The relative inelasticity of the upper section 33A of the pad 33 which is integral with the upper portions of the side sections 33B and 33C of the pad 33 precludes the side sections of the pad, particularly the upper portions thereof, from moving apart significantly when the knee is flexed which, if it occurred, would rearwardly displace or dislocate the side sections of the pad relative to the kneecap.

The pad 33 is loosely mounted to the interior of the sleeve 11 of the region generally surrounding the kneecap opening 30 with the upper 33A portion and opposite side portions 33B and 33C of the pad adjacent at least the top and sides of the opening, respectively, to limitedly variably positionally locate the pad relative to the sleeve kneecap opening to permit the pad to self-align centrally of the wearer's kneecap notwithstanding limited misalignment between the kneecap opening and the wearer's kneecap. Loose mounting of the pad to the interior of the sleeve proximate the kneecap opening 30 to accomplish the self-aligning capability outlined above is achieved, in a preferred form of the invention, by securing, e.g., by stitching, the inner and outer peripheral edges of the pocket 32 to the sleeve at spaced points along the pocket periphery. The points at which the interior pocket 32 is secured to the interior of the sleeve collectively constitutes a small fraction of the inner and outer peripheral edges of the pocket available for securement to the sleeve interior. As a consequence, the pad is positionally shiftable relative to the kneecap opening in the sleeve to permit the pad to self-align centrally of the wearer's kneecap notwithstanding limited non-alignment between the kneecap opening and the wearer's kneecap. For example, in the preferred embodiment of the invention depicted in FIGS. 1-5 the pocket 32 is secured to the interior of the sleeve only at spaced points A-J located along the inner and outer peripheral edges of the pocket.

When the knee brace is applied by a wearer, he slips his foot through the sleeve 11 and pulls on the sleeve to bring it into a position such that the kneecap opening 30 is located approximately centrally of the kneecap. In this position, the upper seam of the sleeve rides above the knee joint and the lower seam of the sleeve resides beneath the knee joint. The springs 21 carried in pockets 12, 13 and 14 engage the lefthand areas of the knee, the most forward of the strips lying over the ligament area adjacent the kneecap, the other strips covering the ligaments on the side of the knee. In a similar manner, springs 21 carried by pockets 15, 16 and 17 cover the ligament area of the knee joint on the righthand front and side of the knee. These spring elements increase the support given to the knee joint even when the knee is straight, since the spring strips rigidify the sleeve and tend to resist any local deformation of the sleeve, thereby applying a greater pressure on the ligament areas.

More importantly, however, when the knee is bent the strips within pockets 12-17 are bent and remain in contact with the knee. When the knee is bent in this manner the forward edge of the sleeve tends to stretch, placing the inelastic pockets in tension. The tension force of these pockets is in turn transmitted evenly to the knee through the spring carried in the pocket.

Additionally, these springs 21 tend to stretch, but the stretching is limited by the spring tension. While the ends of the springs tend to shift within the pockets during bending movement, the friction of the cloth against the spring resists this movement and further augments the pressure applied by the spring to the knee. While the springs 21 apply a firm support to the ligament areas of the knee, the surfaces of the springs remain relatively smooth so that the wearer encounters no discomfort.

At the same time, the circumferential elasticity of the sleeve and spring stays 21 apply pressure ove the entire knee area of the wearer. Simultaneously, the pressure transmitted from the springs through the side sections of the resilient pad 32 applies a localized high pressure over the opposed joint areas of the knee.

The inherent rigidity of this knee brace construction effectively restrains relative lateral and medial rotation of the bones at the knee joint as well as anterior or posterior glide at the joint. Also, the pressure applying pad 32, particularly the side sections thereof, effectively prevent lateral or medial protrusion of the cartilages.

The pad 32 is preferably formed of a suitable flexible resilient, but circumferentially relatively inelastic material, such as "slow rebound" closed cellular polyvinyl chloride foam having a thickness of approximately ⅜. Such a pad, while being compressible in the direction Z (FIG. 4) to temporarily assume varying thicknesses, is not significantly stretchable in a circumferential, knee-encircling direction parallel to the surface of an imaginary cylinder to which the inner pad surface S (FIG. 3) is spatially coincident when the brace is positioned about the wearer's knee. As a consequence, when the knee is flexed the side sections 32B and 32C of the resilient pads 33, particularly the upper regions thereof, do not move rearwardly significantly to dislocate the side portions of the pad relative to the side edges of the kneecap. That is, when the knee is flexed the distance $d$ between the inner peripheral edges of the side sections 32B and 32C of the pad 33 does not significantly increase when the knee is flexed due to the relatively circumferentially inelastic nature of the upper section 33A of the pad 32 which is integral with and joins the upper regions of the side sections 33B and 33C of the pad. As a consequence, the side sections of the pad do not move rearwardly relative to the side edges of the kneecap when the knee is flexed.

The modified knee brace depicted in FIGS. 6 and 7 is identical in all respects to the knee brace depicted in FIGS. 1-5 with one exception. The one exception is that the flexible, resilient, circumferentially relatively inelastic pad 33' and associated pocket 32' is annular. By virtue of the pad 33' being annular, the lower portions of side sections 33B' and 33C' thereof, which are integral with the lower pad section 33D, will, like the upper portions of side sections 33B' and 33C' integral with upper pad section 33A', not move rearwardly significantly when the knee is flexed. This further enhances the tendency of the side sections 33B' and 33C' of the pad 33' to resist movement rearwardly or dislocate relative to the kneecap when the knee is flexed.

Figure 5:
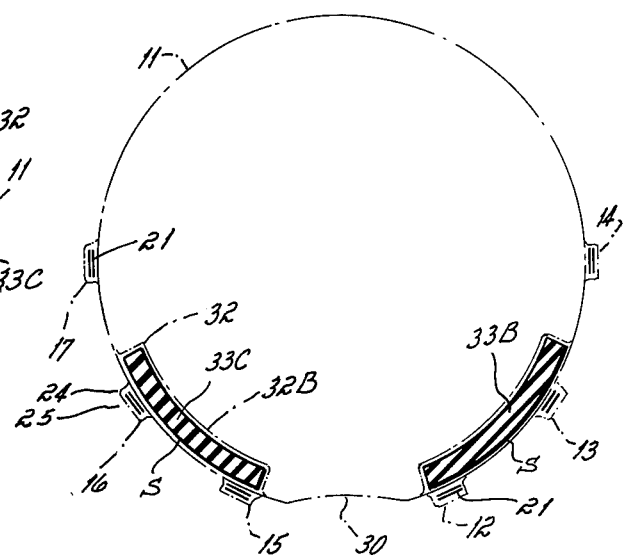
FIG. 5 is a schematic cross-sectional view taken along line 5—5 of FIG. 1.

Like the pad 33 of the embodiment of FIGS. 1-5, the pad 33' depicted in FIGS. 5 and 6 is mounted to the sleeve 11' such that self-alignment of the pad, particularly the central opening thereof, relative to the kneecap occurs notwithstanding misalignment between the wearer's kneecap and the sleeve opening 30'. This is accomplished by stitching the inner and outer peripheral edges of the pocket 32' at spaced points A'-F' along the outer and inner peripheries of the pocket. The stitched points of the peripheral edges of the pad-containing pocket 32' constitutes a small fraction of the available peripheral edge of the pocket for stitching to the sleeve, thereby providing a floating type mount for the pad relative to the kneecap opening 30' in the sleeve 11'. This floating-type mounting arrangement for the annular pad 33' relative to the sleeve kneecap opening 30' permits the pad 33' to symmetrically align itself automatically with the kneecap of the wearer, notwithstanding limited misalignment between the wearer's kneecap and the kneecap opening 30' in sleeve 11'.

The pads 33 and 33' also function to protect the kneecap and area adjacent the wearer's kneecap from injury and/or discomfort induced by impact when the wearer's knee strikes an object.

In accordance with a still further embodiment of the invention a resilient pad 40, constructed of the same material as the inverted C-shaped and annular pads of the aforedescribed embodiments, can be utilized as a substitute for the annular and/or inverted C-shaped pads. The pad 40 includes a generally oval uniform thickness section 41, approximately ⅜ thick, with a kneecap opening 42 provided in the central portion thereof for accommodating the kneecap of a wearer. Formed integral with the uniform thickness resilient pad section 41 of the pads 40 on either side of the opening 42 are arcuate resilient pad sections 44 and 45. Each pad 44 and 45 is beveled, as indicated by the reference "B,"

along its entire periphery. The inner curved beveled edges 44A and 45A of the pad sections 44 and 45 are disposed to snugly embrace the opposite sides of a wearer's kneecap when the pad 40 is mounted interiorly of an elastic sleeve of the type described in connection with the embodiments of FIGS. 1–8. Instead of forming the pad sections 44 and 45 integral with the oval uniform thickness pad section 42, the pad sections 44 and 45 could be fabricated separately and adhered to the surface 41A of the oval uniform thickness pad section 41. The pad sections 44 and 45 provide enhanced comfort and protection for the kneecap of the wearer.

If desired, the pads of this invention may be stitched or tacked directly to the sleeve at peripherally spaced points, rather than enclosed in a pocket, which pocket is stitched to the sleeve.

In practice, it has been found that the pads of this invention, which have a relatively low elasticity relative to the sleeve in the circumferential direction, can be fabricated of Type AAC foam manufactured by Uniroyal, Inc., Expanded Products Department, Mishawaka, Ind., under the trademark Ensolite. Such pad material has a density of 5.0–7.0 pounds per cubic foot and an elongation at breakage of approximately 175%. Such an elongation is relatively low compared to an elongation at breakage of approximately 500 for typical relatively highly elastic sleeve material.

If desired, a strap 20 shown in phantom in FIG. 2 can be provided. The strap 20 is designed to encircle the entire knee brace in the region above the kneecap opening 30 in overlying relationship to the upper central portion of the resilient pad. The strap 20, which is preferably adjustable, when tightened, applies an inward radial compressive force to the region above the wearer's kneecap via the resilient pad. Such pressure has been found to provide improved protection against injury, and in addition tends to stabilize the position of the brace with respect to the knee.

Having described in detail the preferred embodiment of the invention, what is claimed is:

1. An improved knee brace comprising:
    a one piece, continuous, generally cylindrical sleeve formed of elastic material stretchable in a circumferential direction and dimensioned to cover the leg area at the knee joint, said sleeve having a forward section with an opening therein to accommodate the kneecap area of the wearer, a rear section, and oppositely disposed side sections intermediate said forward and rear sections,
    a flexible interior pocket disposed in the interior of the sleeve surrounding said kneecap opening adjacent at least the top and sides of said opening, said flexible pocket being secured to said sleeve,
    a one piece inverted U-shaped resilient flexible pad disposed in said interior pocket and having integral upper and opposite side sections to surround the upper and lateral portions of the wearer's kneecap, respectively, said pad being relatively inelastic compared to said sleeve in a direction circumferentially encircling said knee to resist rearward movement and dislocation relative to the wearer's kneecap of said opposite side pad sections when the wearer's knee is flexed,
    a plurality of longitudinal strips formed of an inelastic material stitched to the forward and side sections of said sleeve on the exterior surface thereof and extending substantially the full length of said sleeve, said strips cooperating with said sleeve to form a plurality of pockets, said pockets disposed on each side of the wearer's knee and being laterally spaced from each other to collectively overlie opposite sides of the wearer's knee from the edges of the kneecap to the ligaments running along the sides of the knee, and
    a plurality of flexible pressure elements, each of said pressure elements comprising two interleaved and overlapping flattened helical springs and end caps for holding said springs in assembled relation, each of said springs being mounted within one of said pockets and extending over a substantial portion of the length of said sleeve.

2. The knee brace of claim 1 wherein said interior pocket has inner and outer peripheral edges and is secured to said sleeve at spaced points along said periphery, the points at which said interior pocket is secured to said sleeve collectively constituting a small fraction of the peripheral edge of said pocket available for securement to said sleeve, whereby said pad is positionally shiftable relative to said kneecap opening in said sleeve to permit said pad to self-align centrally of the wearer's kneecap notwithstanding limited misalignment between said kneecap and the wearer's kneecap.

3. An improved knee brace comprising:
    a one piece, continuous, generally cylindrical sleeve formed of elastic material stretchable in a circumferential direction and dimensioned to cover the leg area at the knee joint, said sleeve having a forward section with an opening therein to accommodate the knee cap area of the wearer, a rear section, and oppositely disposed side sections intermediate said forward and rear sections,
    a inverted U-shaped resilient flexible pad having integral upper and opposite side sections to surround the upper and lateral portions of the wearer's kneecap, respectively, said pad being relatively inelastic compared to said sleeve in a direction circumferentially encircling said knee to resist rearward movement and dislocation relative to the wearer's kneecap of said opposite side pad sections when the wearer's knee is flexed, and
    means to loosely mount said pad in the interior of said sleeve in the region generally surrounding said kneecap opening with the upper and opposite sides of said pad adjacent at least the top and sides of said opening, respectively, to limitedly variably positionally locate said pad relative to said kneecap opening in said sleeve to permit said pad to self-align centrally of the wearer's kneecap notwithstanding limited misalignment between said kneecap opening and said wearer's kneecap.

4. The kneecap of claim 3 wherein said mounting means includes:
    a flexible interior pocket disposed in the interior of the sleeve surrounding said kneecap opening adjacent at least the top and sides of said opening, said flexible pocket being secured to said sleeve, said interior pocket having inner and outer peripheral edges and secured to said sleeve at space points along said periphery, the point at which said interior pocket is secured to said sleeve collectively constituting a small fraction of the peripheral edge of said pocket available for securement to said sleeve, whereby said pad is positionally shiftable relative to said kneecap opening in said sleeve to permit said pad to self-align centrally of the wearer's kneecap notwithstanding limited misalignment between said kneecap opening and the wearer's kneecap.

5. An improved knee brace comprising:

a one piece, continuous, generally cylindrical sleeve formed of elastic material stretchable in a circumferential direction and dimensioned to cover the leg area at the knee joint, said sleeve having a forward section with an opening therein to accommodate the kneecap area of the wearer, a rear section, and oppositely disposed side sections intermediate said forward and rear sections, an annular resilient flexible pad having integral upper, lower and opposite side sections to substantially fully surround the upper, lower and opposite lateral portions of the wearer's kneecap, respectively, said pad being relatively inelastic compared to said sleeve in a direction circumferentially encircling said knee to resist rearward movement and dislocation relative to the wearer's kneecap of said opposite side pad sections when the wearer's knee is flexed, and means to loosely mount said annular pad in the interior of said sleeve in the region generally surrounding said opening, to limitedly variably positionally locate said pad relative to said kneecap opening in said sleeve to permit said pad to self-align centrally of the wearer's kneecap notwithstanding limited misalignment between said kneecap opening and said wearer's kneecap.

6. The kneecap of claim 5 wherein said pad mounting means includes:

a flexible interior pocket disposed in the interior of said sleeve surrounding said kneecap opening adjacent the top, bottom and opposite sides thereof, said flexible pocket being secured to said sleeve, said interior pocket having inner and outer substantially circular peripheral edges and secured to said sleeve at spaced points along said periphery, the points at which said interior pocket is secured to said sleeve collectively constituting a small fraction of the peripheral edge of said pocket available for securement to said sleeve, whereby said pad is positionally shiftable relative to said kneecap opening in said sleeve to permit said pad to self-align centrally of the wearer's kneecap notwithstanding limited misalignment between said kneecap opening and the wearer's kneecap.

7. The knee brace of claim 3 further comprising:

a plurality of longitudinal strips formed of an inelastic material stitched to the forward and side sections of said sleeve on the exterior surface thereof and extending substantially the full length of said sleeve, said strips cooperating with said sleeve to form a plurality of pockets, said pockets disposed on each side of the wearer's knee and being laterally spaced from each other to collectively overlie opposite sides of the wearer's knee from the edges of the kneecap to the ligaments running along the sides of the knee, and a plurality of flexible pressure elements, each of said pressure elements comprising two interleaved and overlapping flattened helical springs and end caps for holding said springs in assembled relation, each of said springs being mounted within one of said pockets and extending over a substantial portion of the length of said sleeve.

8. The kneecap of claim 5 further comprising:

a plurality of longitudinal strips formed of an inelastic material stitched to the forward and side sections of said sleeve on the exterior surface thereof and extending substantially the full length of said sleeve, said strips cooperating with said sleeve to form a plurality of pockets, said pockets disposed on each side of the wearer's knee and being laterally spaced from each other to collectively overlie opposite sides of the wearer's knee from the edges of the kneecap to the ligaments running along the sides of the knee, and a plurality of flexible pressure elements, each of said pressure elements comprising two interleaved and overlapping flattened helical springs and end caps for holding said springs in assembled relation, each of said springs being mounted within one of said pockets and extending over a substantial portion of the length of said sleeve.

9. An improved knee brace comprising:

a one piece, continuous, generally cylindrical sleeve formed of elastic material stretchable in a circumferential direction and dimensioned to cover the leg area at the knee joint, said sleeve having a forward section, a rear section, and oppositely disposed side sections intermediate said forward and rear sections, and an inverted U-shaped resilient flexible pad mounted to the interior of said forward section of said sleeve having integral upper and opposite side sections to surround the upper and lateral portions of the wearer's kneecap, respectively, said pad being relatively inelastic compared to said sleeve in a direction circumferentially encircling said knee to resist rearward movement and dislocation relative to the wearer's kneecap of said opposite side pad sections when the wearer's knee is flexed.

10. An improved knee brace comprising:

a one piece, continuous, generally cylindrical sleeve formed of elastic material stretchable in a circumferential direction and dimensioned to cover the leg area at the knee joint, said sleeve having a forward section with an opening therein to accommodate the knee cap area of the wearer, a rear section, and oppositely disposed side sections intermediate said forward and rear sections, and an annular resilient flexible pad mounted to the interior of said forward section of said sleeve and having integral upper, lower and opposite side sections to substantially fully surround the upper, lower and opposite lateral portions of the wearer's kneecap, respectively, said pad being relatively inelastic compared to said sleeve in a direction circumferentially encircling said knee to resist rearward movement and dislocation relative to the wearer's kneecap of said opposite side pad sections when the wearer's knee is flexed.

11. The knee brace of claim 3 wherein the resilient pad includes first and second inwardly extending projections disposed on opposite sides of the sleeve kneecap opening, said projections contoured along their inner edges to snugly embrace the opposite sides of the kneecap of a wearer to enhance the comfort and protection afforded thereto.

12. The knee brace of claim 5 wherein the resilient pad includes first and second inwardly extending projections disposed on opposite sides of the sleeve kneecap opening, said projections contoured along their inner edges to snugly embrace the opposite sides of the kneecap of a wearer to enhance the comfort and protection afforded thereto.

13. The knee brace of claim 9 wherein the resilient pad includes inwardly extending projections disposed to be positioned on opposite sides of the wearer's kneecap when said knee brace encircles a wearer's knee, said projections contoured along their inner edges to snugly embrace the opposite sides of the kneecap of a wearer to enhance the comfort and protection afforded thereto.

14. The knee brace of claim 10 wherein the resilient pad includes inwardly extending projections disposed to be positioned on opposite sides of the wearer's kneecap when said knee brace encircles a wearer's knee, said projections contoured along their inner edges to snugly embrace the opposite sides of the kneecap of a wearer to enhance the comfort and protection afforded thereto.

* * * * *

UNITED STATES PATENT AND TRADEMARK OFFICE
CERTIFICATE OF CORRECTION

PATENT NO. : 4,116,236
DATED : September 26, 1978
INVENTOR(S) : William J. Albert It is certified that error appears in the above–identified patent and that said Letters Patent are hereby corrected as shown below:

Col. 5 Line 50   "ove"           should be --over--

Col. 5 Line 64   "3/8"           should be --3/8"--

Col. 6 Line 62   "3/8"           should be --3/8"--

Signed and Sealed this

Twenty-seventh Day of March 1979

[SEAL]

Attest:

RUTH C. MASON
Attesting Officer

DONALD W. BANNER
Commissioner of Patents and Trademarks